US008921585B2

(12) United States Patent
Brown

(10) Patent No.: US 8,921,585 B2
(45) Date of Patent: Dec. 30, 2014

(54) METHOD OF SYNTHESIS OF SUBSTITUTED HEXITOLS SUCH AS DIANHYDROGALACTITOL

(71) Applicant: Del Mar Pharmaceuticals, Vancouver (CA)

(72) Inventor: Dennis M. Brown, Menlo Park, CA (US)

(73) Assignee: Del Mar Pharmaceuticals, Vancouver (CA)

( * ) Notice: Subject to any disclaimer, the term of this patent is extended or adjusted under 35 U.S.C. 154(b) by 0 days.

(21) Appl. No.: 13/933,751

(22) Filed: Jul. 2, 2013

(65) Prior Publication Data

US 2014/0155638 A1 Jun. 5, 2014

Related U.S. Application Data

(63) Continuation-in-part of application No. 13/817,046, filed as application No. PCT/US2011/048032 on Aug. 17, 2011.

(60) Provisional application No. 61/401,710, filed on Aug. 18, 2010.

(51) Int. Cl.

| | |
|---|---|
| ***C07D 303/14*** | (2006.01) |
| ***C07D 301/24*** | (2006.01) |
| ***C07D 301/26*** | (2006.01) |
| ***C07D 301/03*** | (2006.01) |
| ***C07D 301/02*** | (2006.01) |

(52) U.S. Cl.
CPC ............ *C07D 301/02* (2013.01); *C07D 301/26* (2013.01); *C07D 301/03* (2013.01)
USPC .......................................... 549/521; 549/555

(58) Field of Classification Search
USPC ................................. 549/523, 554, 521, 555
See application file for complete search history.

(56) References Cited

U.S. PATENT DOCUMENTS

| | | | |
|---|---|---|---|
| 3,470,179 | A | 9/1969 | Ott |
| 3,993,781 | A | 11/1976 | Horvath et al. |
| 7,157,079 | B2 | 1/2007 | Nielsen et al. |
| 2002/0032230 | A1 | 3/2002 | Pal et al. |
| 2002/0037328 | A1 | 3/2002 | Brown |

*Primary Examiner* — T. Victor Oh
(74) *Attorney, Agent, or Firm* — Ditthavong & Steiner, P.C.

(57) ABSTRACT

The present invention provides an efficient method of synthesizing and purifying dianhydrohexitols such as dianhydrogalactitol. In general, as applied to dianhydrogalactitol, the method comprises: (1) reacting dulcitol with a concentrated solution of hydrobromic acid at a temperature of about 80° C. to produce dibromogalactitol; (2) reacting the dibromogalactitol with potassium carbonate in t-butanol to produce dianhydrogalactitol; and (3) purifying the dianhydrogalactitol using a slurry of ethyl ether to produce purified dianhydrogalactitol. Another method produces dianhydrogalactitol from dulcitol; this method comprises: (1) reacting dulcitol with a reactant to convert the 1,6-hydroxy groups of dulcitol to an effective leaving group to generate an intermediate; and (2) reacting the intermediate with an inorganic weak base to produce dianhydrogalactitol through an intramolecular $S_N2$ reaction. Other methods for the synthesis of dianhydrogalactitol from dulcitol are described.

29 Claims, No Drawings

METHOD OF SYNTHESIS OF SUBSTITUTED HEXITOLS SUCH AS DIANHYDROGALACTITOL

CROSS-REFERENCES

This application is a continuation-in-part of U.S. patent application Ser. No. 13/817,046, by Dennis M. Brown, Ph.D., filed Feb. 14, 2013, and entitled "Method of Synthesis of Substituted Hexitols Such as Dianhydrogalactitol,", which in turn claimed the benefit of PCT Application Ser. No. PCT/US2011/048032, by Dennis M. Brown, Ph.D., filed Aug. 17, 2011, designating the United States, and entitled "Method of Synthesis of Substituted Hexitols Such as Dianhydrogalactitol," which in turn claimed the benefit of U.S. Provisional Application Ser. No. 61/401,710, by Dennis M. Brown, Ph.D., filed Aug. 18, 2010, and entitled "Method of Synthesis of Substituted Hexitols Such as Dianhydrogalactitol." These three applications are incorporated herein in their entirety by this reference.

TECHNICAL FIELD OF THE INVENTION

The present invention is directed to improved methods for the synthesis of substituted hexitols, especially dianhydrogalactitol.

BACKGROUND OF THE INVENTION

A number of substituted hexitols, such as dianhydrogalactitol, have pharmacological activities. In particular, dianhydrogalactitol has been suggested for use in chemotherapy, such as in U.S. Pat. No. 7,157,059 to Nielsen et al., incorporated herein by this reference.

However, current methods of synthesis of such substituted hexitols, such as dianhydrogalactitol, are inefficient, and improved methods of synthesis of these substituted hexitols are required in order to provide larger quantities of these compounds for clinical use.

SUMMARY OF THE INVENTION

An improved method of synthesis of dianhydrohexitols such as dianhydrogalactitol comprises conversion of the hexitol to a dibromohexitol by reaction with concentrated hydrobromic acid, followed by conversion of the dibromohexitol to the dianhydrohexitol by reaction with potassium carbonate.

In general, as applied to the synthesis of dianhydrogalactitol, the method comprises the steps of:

(1) reacting dulcitol with a concentrated solution of hydrobromic acid at a temperature of about 80° C. to produce dibromogalactitol;

(2) reacting the dibromogalactitol with potassium carbonate in t-butanol to produce dianhydrogalactitol; and (3) purifying the dianhydrogalactitol using a slurry of ethyl ether to produce purified dianhydrogalactitol.

In this method, typically, the concentrated solution of hydrobromic acid is about 70% hydrobromic acid and is produced by reacting phosphorus with bromine in hydrobromic acid at elevated temperature. Typically, the dibromogalactitol is dissolved in t-butanol in a proportion of about 1 g of dibromogalactitol to 10 mL of t-butanol.

In this method, typically, the dulcitol is purified from the plant *Maytenus confertiflora* by the steps of:

(a) soaking the plant *Maytenus confertiflora* in a soaking solution of from about 50% to about 80% of ethanol for about 24 hours;

(b) collecting the soaking solution from step (a);

(c) repeating the soaking step of step (a) with a fresh soaking solution of from about 50% to about 80% of ethanol for about 24 hours;

(d) collecting the soaking solution from step (c) and combining it with the soaking solution collected in step (b);

(e) removing the solvent from the combined soaking solutions of step (d) by heating under reduced pressure to produce a concentrated solution;

(f) allowing the concentrated solution of step (e) to settle overnight and collecting the clear supernatant;

(g) extracting the clear supernatant from step (f) with chloroform and then removing the chloroform under heat and reduced pressure;

(h) dissolving the residue from step (g) in hot methanol and then cooling to allow crystallization; and (i) collecting the collected crystals of dulcitol, filtering, and drying the crystals under reduced pressure.

Although this method is described for the synthesis and purification of dianhydrogalactitol, it is not limited to dianhydrogalactitol, and can be applied to other hexitols bearing two epoxide groups such as substituted dianhydrogalactitols.

More generally, a method according to the present invention for synthesizing and purifying a dianhydrohexitol comprises the steps of:

(1) reacting a hexitol bearing two epoxide groups with a concentrated solution of hydrobromic acid at a temperature of about 80° C. to produce a dibromohexitol;

(2) reacting the dibromohexitol with a carbonate salt of an alkali metal in a tertiary alcohol to produce a dianhydrohexitol; and (3) purifying the dianhydrohexitol using a slurry of an ether to produce the purified dianhydrohexitol.

Typically, the dianhydrohexitol is selected from the group consisting of dianhydrogalactitol and a substituted dianhydrogalactitol. Preferably, the dianhydrohexitol is dianhydrogalactitol.

Typically, the concentrated solution of hydrobromic acid is about 70% hydrobromic acid and is produced by reacting phosphorus with bromine in hydrobromic acid at elevated temperature.

Typically, the tertiary alcohol is selected from the group consisting of t-butanol, 2-methyl-2-butanol, and 3-ethylpentanol. Preferably, the tertiary alcohol is t-butanol.

Typically, the dibromohexitol is dissolved in the tertiary alcohol in a proportion of about 1 g of dibromohexitol to 10 mL of tertiary alcohol.

Typically, the dibromohexitol is purified by recrystallization prior to its conversion to dianhydrohexitol.

Typically, the carbonate salt of the alkali metal is a carbonate salt of an alkali metal selected from the group consisting of sodium carbonate and potassium carbonate. Preferably, the carbonate salt of the alkali metal is potassium carbonate.

Typically, the ether is an aliphatic ether with lower alkyl groups. Preferably, the ether is selected from the group consisting of dimethyl ether, methyl ethyl ether, diethyl ether, dipropyl ether, methyl propyl ether, and ethyl propyl ether. More preferably, the ether is diethyl ether.

Other methods for the synthesis of dianhydrogalactitol are described. In general, these methods start with dulcitol.

In one alternative, the method comprises:

(1) reacting dulcitol with a reactant to convert the 1,6-hydroxy groups of dulcitol to an effective leaving group to generate an intermediate; and (2) reacting the intermediate with an inorganic weak base to produce dianhydrogalactitol through an intramolecular $S_N2$ reaction.

Typically, the effective leaving group of step (1) is selected from the group consisting of Br, OTf (triflate or trifluoromethane sulfonate), and OTs (tosylate). Preferably, the effective leaving group of step (1) is Br.

In one alternative, the intermediate of step (1) is prepared by:

(a) using 45-48% aqueous hydrobromic acid with the addition of phosphorus and $Br_2$ to generate a 60-70% solution of hydrobromic acid, then adding dulcitol and reacting at 70° C. for 5-7 hours;

(b) cooling the reaction mass of (i) to room temperature and pouring into ice water to obtain the crude intermediate of step (1); and (c) recrystallizing using a polar solvent without a nucleophilic property.

In another alternative, the intermediate of step (1) is prepared by:

(a) adding dulcitol to a 62% aqueous hydrobromic acid solution and reacting at 70° C. for 5-7 hours;

(b) cooling the reaction mass of (a) to room temperature and pouring into ice water to obtain the crude intermediate of step (1); and (c) recrystallizing using a polar solvent without a nucleophilic property.

In yet another alternative, the intermediate of step (1) is prepared by:

(a) adding dulcitol to a 33% HBr solution in acetic acid and mixing for 5-7 hours at room temperature;

(b) adding methanol and mixing for 15 hours;

(c) concentrating under vacuum to remove most of the solvent;

(d) recrystallizing using a polar solvent without a nucleophilic property.

In still another alternative, the intermediate of step (1) is prepared by:

(a) dissolving dulcitol in pyridine or dimethylformamide (DMF) at room temperature;

(b) adding $CBr_4$ and $Ph_3P$ in sequence and mixing for 15-18 hours at room temperature;

(c) after the completion of the reaction of step (ii), concentrating under vacuum to remove solvent and chloroform formed from the reaction;

(d) washing the remaining solid several times with dichloromethane to remove triphenylphosphine byproduct; and (e) recrystallizing using a polar solvent without a nucleophilic property. Typically, in this alternative, the dulcitol is dissolved in pyridine. Alternatively, the dulcitol is dissolved in dimethylformamide.

Typically, the polar solvent without a nucleophilic property is selected from the group consisting of 2-chloromethane/t-butanol and 2-chloromethane/isopropyl alcohol.

When the effective leaving group of step (1) is selected from the group consisting of OTf (triflate or trifluoromethane sulfonate) and OTs (tosylate), typically, the intermediate is generated by:

(a) dissolving dulcitol in pyridine;

(b) adding TsCl or $Tf_2O$ at 0° C. and mixing for 15-18 hours;

(c) after the completion of the reaction, concentrating under vacuum to remove solvent;

(d) pouring the remaining solution into ice water to obtain the intermediate; and (e) recrystallizing using a polar solvent without a nucleophilic property.

In one alternative, the intermediate is converted to DAG using $K_2CO_3$ and t-BuOH.

In another alternative, the intermediate is converted to DAG using an inorganic alkali in a polar nonionic solvent. In this alternative, typically, the intermediate is converted to DAG employing a process with the steps of:

(a) dissolving the intermediate in the polar nonionic solvent;

(b) adding an inorganic carbonate and mixing at room temperature for 5-7 hours;

(c) after the completion of the reaction of step (ii), adding p-toluenesulfonic acid to neutralize the inorganic carbonate;

(d) concentrating under vacuum to remove the solvent;

(e) washing the remaining solid with water to remove impurities;

(f) adding ether to the crude material of step (v); and (g) filtering the slurry to obtain DAG.

Typically, the inorganic carbonate is selected from the group consisting of $K_2CO_3$ and $Cs_2CO_3$. Preferably, the inorganic carbonate is $K_2CO_3$. Typically, the polar nonionic solvent is dimethylformamide (DMF).

Another aspect of the invention is a method for synthesizing dianhydrogalactitol (DAG) comprising the steps of:

(1) substituting the 1,6-hydroxyl groups of dulcitol with bromine;

(2) substituting the hydroxyl groups of dulcitol other than the 1,6-hydroxyl groups with acetyl groups to yield an intermediate in which the 1,6-hydroxyl groups of dulcitol are substituted with bromine and the hydroxyl groups of dulcitol other than the 1,6-hydroxyl groups are substituted with acetyl groups;

(3) reacting the intermediate of step (2) with zinc in the presence of an organic base to form double bonds through an elimination reaction;

(4) removing the protective acetyl groups; and (5) forming dianhydrogalactitol by the Sharpless epoxidation reaction.

Typically, the organic base is sodium methoxide. Typically, the substitution of the 1,6 hydroxy groups is performed with reaction with acetyl bromide. Typically, the acetylation of the hydroxy groups other than the 1,6-hydroxy groups is performed with acetic anhydride in pyridine.

DETAILED DESCRIPTION OF THE INVENTION

Dianhydrogalactitol (DAG) can be synthesized from dulcitol which can be produced from natural sources (such as *Maytenus confertiflora*) or commercial sources.

The structure of DAG is given below as Formula (I).

(I)

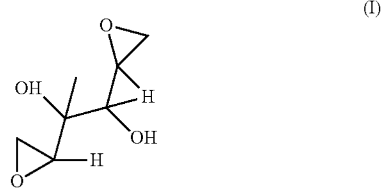

One method for the preparation of dulcitol from *Maytenus confertiflora* is as follows: (1) The *Maytenus confertiflora* plant is soaked in diluted ethanol (50-80%) for about 24 hours, and the soaking solution is collected. (2) The soaking step is repeated, and all soaking solutions are combined. (3)

The solvent is removed by heating under reduced pressure. (4) The concentrated solution is allowed to settle overnight and the clear supernatant is collected. (5) Chloroform is used to extract the supernatant. The chloroform is then removed under heat and reduced pressure. (6) The residue is then dissolved in hot methanol and cooled to allow crystallization. (7) The collected crystals of dulcitol are filtered and dried under reduced pressure. The purified material is dulcitol, contained in the original *Maytenus confertiflora* plant at a concentration of about 0.1% (1/1000).

In one alternative, DAG can be prepared by two general synthetic routes as described below:

Route 1:

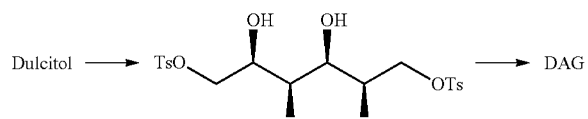

Route 2:

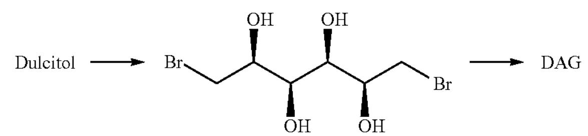

In Route 1, "Ts" represents the tosyl group, or p-toluenesulfonyl group.

However, the intermediate of Route 1, 1,6-ditosyldulcitol, was prepared with low yield (~36%), and the synthesis of 1,6-ditosyldulcitol was poorly reproducible. Therefore, the second route process was developed, involving two major steps: (1) preparation of dibromodulcitol from dulcitol; and (2) preparation of dianhydrodulcitol from dibromodulcitol.

Dibromodulcitol is prepared from dulcitol as follows: (1) With an aqueous HBr solution of approximately 45% HBr concentration, increase the HBr concentration to about 70% by reacting phosphorus with bromine in concentrated HBr in an autoclave. Cool the solution to 0° C. The reaction is: $2P+3Br_2 \rightarrow 2PBr_3+H_2O \rightarrow HBr\uparrow+H_3PO_4$. (2) Add the dulcitol to the concentrated HBr solution and reflux at 80° C. to complete the reaction. (3) Cool the solution and pour the mixture onto ice water. Dibromodulcitol is purified through recrystallization.

The results for the preparation of dibromodulcitol (DBD) are shown in Table 1, below.

TABLE 1

| | | | | |
|---|---|---|---|---|
| Dulcitol | 18 g | 18 g | 18 g | 18 g |
| 45% aq. HBr | 36 mL | 36 mL | 36 mL | 36 mL |
| $PBr_3$ | 40 g | 40 g | 40 g | 40 g |
| Time | 7 h | 7 h | 7 h | 7 h |
| Temp/° C. | 70 | 70 | 70 | 70 |
| Crude Product | 25.2 g | 25.5 g | 24 g | 24.7 g |
| Yield | 84% | 85% | 80% | 82% |

For the preparation of DAG from DBD, DBD was poorly dissolved in methanol and ethanol at 40° C. (different from what was described in U.S. Pat. No. 3,993,781 to Horvath nee Lengyel et al., incorporated herein by this reference). At refluxing, DBD was dissolved but TLC showed that new impurities formed that were difficult to remove from DBD.

The DBD was reacted with potassium carbonate to convert the DBD to dianhydrogalactitol.

The results are shown in Table 2, below.

TABLE 2

| | | | |
|---|---|---|---|
| DBD | 0.5 g | 5 g | 4.3 g |
| $K_2CO_3$ | 1 g | 8 g | 4 g |
| t-BuOH | 5 mL | 50 mL | 40 mL |
| DAG | 0.17 g | 1 g | 0.82 g |
| Yield | 72% | 42% | 40% |

In the scale-up development, it was found the crude yield dropped significantly. It is unclear if DAG could be azeotropic with BuOH. It was confirmed that t-BuOH is essential to the reaction. Using MeOH as solvent would result in many impurities as shown spots on TLC. However, an improved purification method was developed by using a slurry with ethyl ether, which could provide DAG with good purity. This was developed after a number of failed attempts at recrystallization of DAG.

Accordingly, one aspect of the present invention is a method for synthesizing and purifying dianhydrogalactitol (DAG) comprising the steps of:

(1) reacting dulcitol with a concentrated solution of hydrobromic acid at a temperature of about 80° C. to produce dibromogalactitol;

(2) reacting the dibromogalactitol with potassium carbonate in t-butanol to produce dianhydrogalactitol; and (3) purifying the dianhydrogalactitol using a slurry of ethyl ether to produce purified dianhydrogalactitol.

In this method, typically, the concentrated solution of hydrobromic acid is about 70% hydrobromic acid and is produced by reacting phosphorus with bromine in hydrobromic acid at elevated temperature. Typically, the dibromogalactitol is dissolved in t-butanol in a proportion of about 1 g of dibromogalactitol to 10 mL of t-butanol. Typically, the dibromogalactitol is purified by recrystallization prior to its conversion to dianhydrogalactitol.

In this method, typically, the dulcitol is purified from the plant *Maytenus confertiflora* by the steps of:

(a) soaking the plant *Maytenus confertiflora* in a soaking solution of from about 50% to about 80% of ethanol for about 24 hours;

(b) collecting the soaking solution from step (a);

(c) repeating the soaking step of step (a) with a fresh soaking solution of from about 50% to about 80% of ethanol for about 24 hours;

(d) collecting the soaking solution from step (c) and combining it with the soaking solution collected in step (b);

(e) removing the solvent from the combined soaking solutions of step (iv) by heating under reduced pressure to produce a concentrated solution;

(f) allowing the concentrated solution of step (e) to settle overnight and collecting the clear supernatant;

(g) extracting the clear supernatant from step (f) with chloroform and then removing the chloroform under heat and reduced pressure;

(h) dissolving the residue from step (g) in hot methanol and then cooling to allow crystallization; and (i) collecting the collected crystals of dulcitol, filtering, and drying the crystals under reduced pressure.

Another embodiment of the invention is a method for synthesizing and purifying a dianhydrohexitol comprising the steps of:

(1) reacting a hexitol bearing two epoxide groups with a concentrated solution of hydrobromic acid at a temperature of about 80° C. to produce a dibromohexitol;

(2) reacting the dibromohexitol with a carbonate salt of an alkali metal in a tertiary alcohol to produce a dianhydrohexitol; and (3) purifying the dianhydrohexitol using a slurry of an ether to produce the purified dianhydrohexitol.

In this method, the dianhydrohexitol can be, for example, dianhydrogalactitol or another dianhydrohexitol that has two epoxide groups, such as a substituted dianhydrogalactitol, as described above. However, typically the dianhydrohexitol is dianhydrogalactitol.

In this method, the carbonate salt of the alkali metal is typically a carbonate salt of an alkali metal selected from the group consisting of sodium carbonate and potassium carbonate. Preferably, the carbonate salt of the alkali metal is potassium carbonate.

In this method, the tertiary alcohol is typically t-butanol; however, other tertiary alcohols can be alternatively employed. Such tertiary alcohols include, for example, 2-methyl-2-butanol, 3-ethylpentanol, and other tertiary alcohols, typically containing 6 carbons or fewer.

In this method, the debromination step (step (2) above) occurs under refluxing conditions, which means that, when the tertiary alcohol is t-butanol, which has a boiling point of 82° C., reflux temperature would be about 80-85° C.

In this method, in the step of purifying the dianhydrohexitol from the ether slurry (step (3) above), the ether is typically an aliphatic ether with lower alkyl groups, such as dimethyl ether, methyl ethyl ether, diethyl ether, dipropyl ether, methyl propyl ether, and ethyl propyl ether. However, a preferable ether is diethyl ether.

Additional alternatives for the synthesis of dianhydrogalactitol are described. In general, in these alternatives, dianhydrogalactitol synthesis involves three major steps: (1) preparation of dibromodulcitol (DBD) from a commercial source of dulcitol; (2) preparation of dianhydrogalactitol (DAG) from DBD; and (3) recrystallization to purify the DAG.

The specific process for each step is described below:

For the preparation of DBD, the reaction is as shown in Scheme 1 (Step 1), below:

Scheme 1 (Step 1)

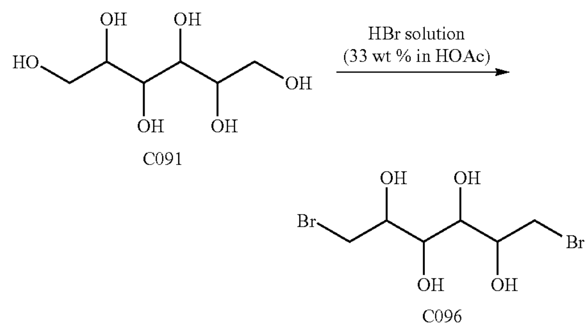

Hydrobromic acid (33% HBr in acetic acid, 2.1 eq) was added to 50 g of dulcitol (1 eq) and mixed. The mixture was then heated to 40° C. and mixed for 18 hours yielding a turbid suspension. The suspension was cooled to room temperature. Water (2 parts) was added and mixed for 18-24 hours and then filtered through a Buchner funnel. The collected solid was washed with water (4 parts) and dried under vacuum and nitrogen for 2 days to obtain off-white to light brown solid (DBD), 34 g or about 40% yield.

This method can be modified according by the use of alternatives known to those of ordinary skill in the art. For example, a relatively low-molecular-weight monoprotic acid such as formic acid or propanoic acid can replace acetic acid.

For the preparation of dianhydrogalactitol from dibromodulcitol, the reaction is as shown in Scheme 2 (Step 2).

Scheme 2 (Step 2)

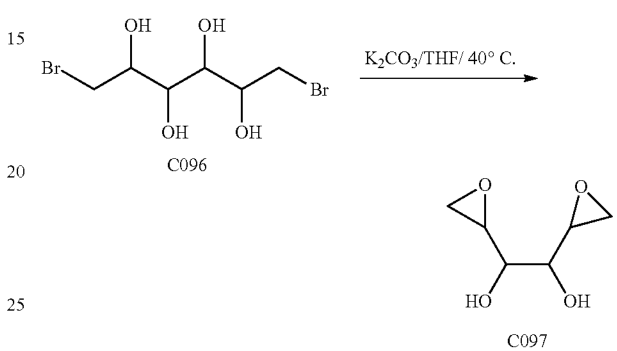

In this method 56 g (2.5 eq) potassium carbonate and THF (tetrahydrofuran) (15 parts) were added to 50 g of DBD (1 eq) and mixed. The mixture was heated to 40° C. and mixed for 18 hours and then cooled to room temperature. The product was filtered through Buchner funnel to remove inorganic solid and washed twice with THF. The filtrate and washes were collected and concentrated to 4-5 parts with water bath set at 35° C. Heptane (10 parts) was added and mixed for 1-2 hours at room temperature. The mixture was filtered through Buchner funnel and washed twice with heptane. The solid was dried under vacuum and nitrogen for 18-24 hours at room temperature to obtain 19 g crude DAG, about 80% yield.

The final step is recrystallization of DAG. THF (20 parts) was added to 18.5 g of crude DAG (1 eq) and mixed for 1-2 hours at room temperature. The mixture was filtered through a Buchner funnel to discard solid. Heptane (20 parts) was slowly added and mixed for 2-4 hours at room temperature. The mixture was filtered. The solid was dried under vacuum and nitrogen for 18-24 hours at room temperature to obtain 10 g crude DAG, about 54% yield.

In this method, other nonpolar organic solvents, typically saturated hydrocarbons such as hexane or octane, can be used in place of heptane. In this methods, other relatively polar but aprotic organic solvents can be used in place of tetrahydrofuran.

Other alternative methods for preparation of DAG are described below. 1,2:5,6-dianhydrodulcitol (also known as DAG) is a compound with multiple hydroxyl groups and epoxide groups. This characteristic structure determines instability of this compound because of the tendency of the epoxide ring to open under acid, base or heat conditions. These methods start with dulcitol rather than dibromodulcitol.

In one additional alternative, the 1,6-hydroxy groups on dulcitol (available commercially) are modified to convert to an effective leaving group such as Br (compound 1 a), OTf (triflate or trifluoromethane sulfonate) (compound lb), or OTs (tosylate) (compound 1c), and then, using an inorganic weak base, the target compound DAG is prepared through an intramolecular SN2 reaction as shown in Scheme 3.

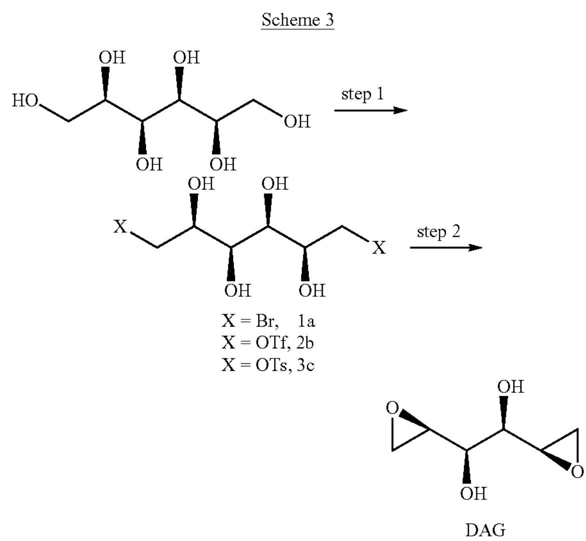

In this alternative, a preferred leaving group is Br. For Step 1 as shown in Scheme 3, there are four possible methods to prepare the intermediate with four hydroxyl groups and two leaving groups (e.g., Br). These methods are as follows when Br is to be introduced as the leaving group. This intermediate is designated Compound 1a below:

Method A for Preparation of Intermediate

The conditions are 45-48% HBr aq/P/$Br_2$/70° C., 5-7 hr. The procedure is as follows: Add phosphorus to aqueous solution of 45-48% HBr at 0° C. and carefully add $Br_2$ drop-wise to make HBr solution with concentration about 60-70%. Add dulcitol and heat to 70° C. in a closed reactor for 5-7 hours. After the completion of reaction, cool the reaction mass to room temperature and pour into ice water to obtain the crude compound 1a (the intermediate referred to above). For purification, a polar solvent without a nucleophilic property, such as 2-chloromethane/t-butanol or 2-chloromethane/isopropyl alcohol is used for recrystallization. Due to the instability of compound 1, (hydrolysis under $D_2O$/room temp or $H_2O$/reverse) back to dulcitol, it is important to avoid hydrolysis so that Compound 1a is not converted back to dulcitol in the course of recrystallization or column chromatography.

This method has high yield (~80%) with good repeatability. However, it requires the use of corrosive HBr solution and volatile, toxic $Br_2$.

Method B for Preparation of Intermediate

The conditions are 62% HBr aq/P/$Br_2$/70° C., 5-7 hr. The procedure is as follows: Add dulcitol to 62% HBr aqueous solution. Heat to 70° C. in a closed reactor for 5-7 hours. After the completion of reaction, cool the reaction mass to room temperature and pour into ice water to obtain the crude Compound 1a. For purification, use mixed solvents of 2-chloromethane/t-butanol or 2-chloromethane/isopropyl alcohol for recrystallization.

This method uses commercial 62% HBr aqueous solution to simplify the procedures and avoid high risk using $Br_2$. However, the reaction needs high corrosive HBr solution and volatile, toxic $Br_2$.

Method C for Preparation of Intermediate

The conditions are 33% HBr in HOAc/r.t., 5-7 hr. The procedure is as follows: Add dulcitol to 33% HBr solution in acetic acid, mix for 5-7 hours at room temperature. Add methanol and mix for 15 hours. Concentrate under vacuum to remove most of the solvent. Pour the remaining solution into ice water to collect the crude Compound 1a. For purification, use mixed solvents of 2-chloromethane/t-butanol or 2-chloromethane/isopropyl alcohol for recrystallization.

This alternative uses commercial 33% HBr acetic solution with simple procedures. However, the reaction requires use of highly corrosive HBr solution.

Method D for Preparation of Intermediate

The conditions are: $CBr_4$/$Ph_3P$/pyridine or DMF/r.t., 15-18 hr. The procedure is as follows: Dissolve dulcitol in pyridine or dimethylformamide (DMF) at room temperature. Add $CBr_4$ and $Ph_3P$ in sequence and mix for 15-18 hours at room temperature. After the completion of reaction, concentrate under vacuum to remove solvent and chloroform formed from reaction. Wash the remaining solid several times with dichloromethane to remove triphenylphosphine byproduct. For purification, use mixed solvents of 2-chloromethane/t-butanol or 2-chloromethane/isopropyl alcohol for recrystallization.

The advantages of this method are moderate reaction conditions without using HBr or $Br_2$. However, the reaction will produce triphenylphosphine byproduct which will affect the purity of Compound 1a.

As indicated above, the 1,6-hydroxy groups can be modified by other leaving groups, such as TfO—(Compound 1b) or TsO—(Compound 1c) in Step 1. Since there are several hydroxyl groups in dulcitol, it is important to control the reagent quantity during sulfonylation reaction.

For the preparation of Compound 1b or Compound 1c, the conditions are: TsCl or $Tf_2O$/Pyridine/0° C., 4-8 hr. The procedure is as follows: Dissolve dulcitol in pyridine. Add TsCl or $Tf_2O$ at 0° C. and mix for 15-18 hours. After the completion of reaction, concentrate under vacuum to remove solvent. Pour the remaining solution into ice water to obtain crude Compound 1b or Compound 1c. For purification, use mixed solvents of 2-chloromethane/t-butanol or 2-chloromethane/isopropyl alcohol for recrystallization.

Typically, this method generates an equivalent of the pyridine salt of p-toluenesulfonic acid or trifluoromethanesulfonic acid. Removal of these byproducts is important in yielding Compound 1b or Compound 1c in high purity.

For Step 2 of this procedure, resulting in DAG, one alternative, described above, uses conditions of $K_2CO_3$/t-BuOH. However, this may not be optimum in larger-scale preparations. Under small scale conditions (0.5 g), moderate yield (~70%) can be achieved. The yield was significantly reduced to ~40% when the scale was 4 g. Although Applicant does not intend to be bound by this supposition, this may result from the formation of an azeotropic mixture of DAG and t-butanol with a low boiling point. Therefore, as indicated above, this may not be efficiently scalable for preparations >1 g.

Under alkaline conditions, Compound 1a, 1b, or 1c, described above (the intermediate prior to the formation of DAG) may undergo a series of side reactions shown in Scheme 4.

Scheme 4

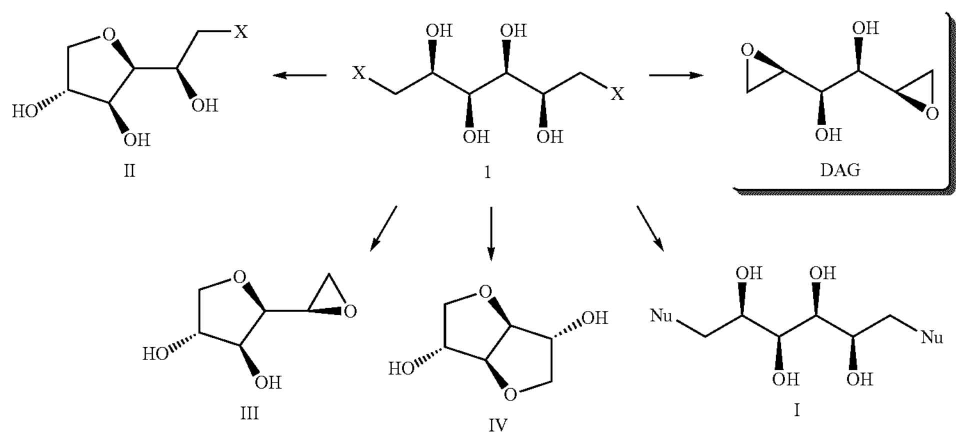

These side reactions may include intermolecular reactions due to nucleophilic reagent of alkaline or solvent (alcohol or water) to produce side product I; or intra-molecular attack by hydroxyl group to produce byproducts (I-IV) with furan ring, formed more rapidly compared to epoxide. Therefore, it is critical to select or control the step 2 reaction conditions to prevent the occurrence of side reactions to the extent possible.

In this alternative, it is generally preferred to use an inorganic alkali (such as $K_2CO_3$, $Cs_2CO_3$, or other inorganic carbonates) and a polar nonionic solvent favorable for $S_N2$ reaction to produce DAG as target product. The inorganic alkali used is not nucleophilic and does not cause intermolecular nucleophilic substitution. The polar nonionic solvent not only provides better solubility for inorganic alkali and a more polar alcohol reactant 1a, 1b, or 1c, but also will not cause side reactions because of the lack of nucleophilicity. In addition, replacing the reported t-butanol with this solvent, the co-distillation (azeotrope formation) between DAG and t-butanol can be avoided. This will resolve the scale-up issue. The specific conditions are as follows: $K_2CO_3$/DMF/r.t., 5-7 hr. The procedure is as follows: Dissolve the product from Step 1 (i.e., Compound 1a, Compound 1b, or Compound 1c), in a polar nonionic solvent such as DMF. Add $K_2CO_3$ or the other inorganic carbonate and mix at room temperature for 5-7 hours. After completion of the reaction, add p-toluenesulfonic acid to neutralize potassium carbonate or other inorganic carbonate. Concentrate under vacuum to remove solvent. Wash the remaining solid with water to remove the inorganic impurities. For purification, add ether to crude material and mix vigorously. Filter the slurry to obtain target DAG.

In another alternative, the synthetic route for dianhydrogalactitol is as shown in Scheme 5.

Scheme 5

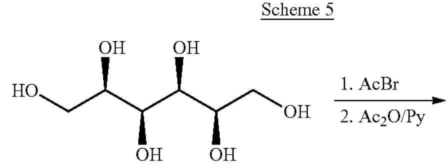

-continued

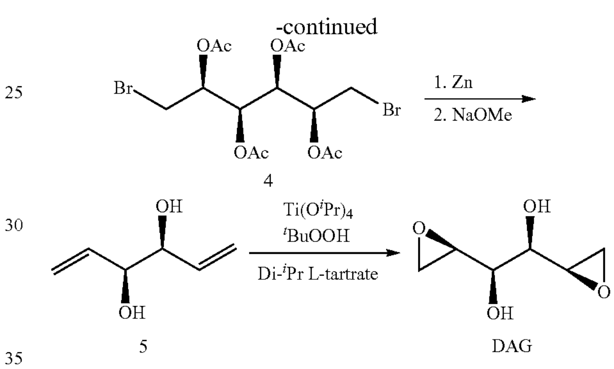

In the synthetic route of Scheme 5, the process starts with substitution of 1,6 hydroxy groups with bromine and other hydroxyl groups with acetyl groups yielding compound 4, which is then reacted with zinc to form double bonds through an elimination reaction with a molecular conjugated base such as sodium methoxide. The protective acetyl group is removed to yield compound 5. Finally, through the use of the Sharpless epoxidation reaction, the target compound DAG is formed. Typically, the substitution of the 1,6 hydroxy groups is performed with reaction with acetyl bromide; alternatively, other bromide-substituted acyl compounds can be used. Typically, the acetylation of the hydroxy groups other than the 1,6-hydroxy groups is performed with acetic anhydride in pyridine.

ADVANTAGES OF THE INVENTION

The present invention provides an improved and efficient method for the synthesis of substituted hexitols, especially dianhydrogalactitol (DAG). The method of the present invention is readily scalable so that large quantities of dianhydrogalactitol can be prepared for pharmaceutical or other use. The method of the present invention produces dianhydrogalactitol in high yield and free from impurities.

Methods according to the present invention possess industrial applicability for the synthesis of substituted hexitols, especially dianhydrogalactitol (DAG), which have uses in pharmacology and elsewhere.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, and literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. A method for synthesizing dianhydrogalactitol (DAG) using dulcitol as a starting material comprising the steps of:

(a) reacting dulcitol with hydrobromic acid (HBr), carbon tetrabromide ($CBr_4$) and triphenylphosphine ($Ph_3P$), para-toluenesulfonyl chloride (tosyl chloride), or trifluoromethanesulfonic anhydride (triflic anhydride) to convert the 1,6-hydroxy groups of dulcitol to 1,6-dibromo, 1,6-ditosylate, or 1,6-ditriflate groups, which provides 1,6-dibromodulcitol, 1,6-ditosyldulcitol or 1,6-ditriflatedulcitol; and (b) reacting the 1,6-dibromodulcitol, 1,6-ditosyldulcitol, or 1,6-ditriflatedulcitol with an inorganic weak base to produce DAG through an intramolecular $S_N2$ reaction.

2. The method of claim 1 wherein the 1,6-hydroxy groups of dulcitol of step (a) are converted to 1,6-dibromo groups.

3. The method of claim 1 wherein the 1,6-hydroxy groups of dulcitol of step (a) are converted to 1,6-ditriflate groups.

4. The method of claim 1 wherein the 1,6-hydroxy groups of dulcitol of step (a) are converted to 1,6-ditosylate groups.

5. The method of claim 2 wherein 1,6-dibromodulcitol of step (a) is prepared by:

(i) using 45-48% aqueous hydrobromic acid with the addition of phosphorus and $Br_2$ to generate a 60-70% solution of hydrobromic acid, then adding dulcitol and reacting at 70° C. for 5-7 hours;

(ii) cooling the reaction mass of (i) to room temperature and pouring into ice water to obtain the crude 1,6-dibromodulcitol of step (a); and (iii) recrystallizing using a polar solvent without a nucleophilic property.

6. The method of claim 5 wherein the polar solvent without a nucleophilic property is selected from the group consisting of 2-chloromethane/t-butanol and 2-chloromethane/isopropyl alcohol.

7. The method of claim 2 wherein 1,6-dibromodulcitol of step (a) is prepared by:

(i) adding dulcitol to a 62% aqueous hydrobromic acid solution and reacting at 70° C. for 5-7 hours;

(ii) cooling the reaction mass of (i) to room temperature and pouring into ice water to obtain the crude 1,6-dibromodulcitol of step (a); and (iii) recrystallizing using a polar solvent without a nucleophilic property.

8. The method of claim 7 wherein the polar solvent without a nucleophilic property is selected from the group consisting of 2-chloromethane/t-butanol and 2-chloromethane/isopropyl alcohol.

9. The method of claim 2 wherein 1,6-dibromodulcitol of step (a) is prepared by:

(i) adding dulcitol to a 33% HBr solution in acetic acid and mixing for 5-7 hours at room temperature;

(ii) adding methanol and mixing for 15 hours;

(iii) concentrating under vacuum to remove most of the solvent to obtain the crude 1,6-dibromodulcitol of step (a);

(iv) recrystallizing using a polar solvent without a nucleophilic property.

10. The method of claim 9 wherein the polar solvent without a nucleophilic property is selected from the group consisting of 2-chloromethane/t-butanol and 2-chloromethane/isopropyl alcohol.

11. The method of claim 2 wherein the intermediate 1,6-dibromodulcitol of step (a) is prepared by:

(i) dissolving dulcitol in pyridine or dimethylformamide (DMF) at room temperature;

(ii) adding $CBr_4$ and $Ph_3P$ in sequence and mixing for 15-18 hours at room temperature;

(iii) after the completion of the reaction of step (ii), concentrating under vacuum to remove solvent and chloroform formed from the reaction;

(iv) washing the remaining solid several times with dichloromethane to remove triphenylphosphine byproduct; and (v) recrystallizing using a polar solvent without a nucleophilic property.

12. The method of claim 11 wherein the polar solvent without a nucleophilic property is selected from the group consisting of 2-chloromethane/t-butanol and 2-chloromethane/isopropyl alcohol.

13. The method of claim 11 wherein the dulcitol is dissolved in pyridine.

14. The method of claim 11 wherein the dulcitol is dissolved in dimethylformamide.

15. The method of claim 1 wherein the 1,6-hydroxy groups of dulcitol of step (a) are converted to 1,6-ditosylate or 1,6-ditriflate groups.

16. The method of claim 15 wherein 1,6-ditosyldulcitol or 1,6-ditriflatedulcitol of step (a) is generated by:

(i) dissolving dulcitol in pyridine;

(ii) adding para-toluenesulfonyl chloride (tosyl chloride) or trifluoromethanesulfonic anhydride (triflic anhydride) at 0° C. and mixing for 15-18 hours;

(iii) after the completion of the reaction, concentrating under vacuum to remove solvent;

(iv) pouring the remaining solution into ice water to obtain the crude 1,6-ditosyldulcitol or 1,6-ditriflatedulcitol of step (a); and (v) recrystallizing using a polar solvent without a nucleophilic property.

17. The method of claim 16 wherein tosyl chloride is added in step (ii).

18. The method of claim 16 wherein triflic anhydride is added in step (ii).

19. The method of claim 16 wherein the polar solvent without a nucleophilic property is selected from the group consisting of 2-chloromethane/t-butanol and 2-chloromethane/isopropyl alcohol.

20. The method of claim 1 wherein 1,6-dibromodulcitol, 1,6-ditosyldulcitol or 1,6-ditriflatedulcitol is converted to DAG using $K_2CO_3$ and t-BuOH.

21. The method of claim 1 wherein 1,6-dibromodulcitol, 1,6-ditosyldulcitol or 1,6-ditriflatedulcitol is converted to DAG using an inorganic alkali in a polar nonionic solvent.

22. The method of claim 21 wherein 1,6-dibromodulcitol, 1,6-ditosyldulcitol, or 1,6-ditriflatedulcitol is converted to DAG employing a process with the steps of:

(i) dissolving the 1,6-dibromodulcitol, 1,6-ditosyldulcitol, or 1,6-ditriflatedulcitol in the polar nonionic solvent;

(ii) adding an inorganic carbonate and mixing at room temperature for 5-7 hours;

(iii) after the completion of the reaction of step (ii), adding p-toluenesulfonic acid to neutralize the inorganic carbonate;

(iv) concentrating under vacuum to remove the solvent;

(v) washing the remaining solid with water to remove impurities;

(vi) adding ether to the crude material of step (v); and (vi) filtering the slurry to obtain DAG.

23. The method of claim 22 wherein the inorganic carbonate is selected from the group consisting of $K_2CO_3$ and $Cs_2CO_3$.

24. The method of claim 23 wherein the inorganic carbonate is $K_2CO_3$.

25. The method of claim 22 wherein the polar nonionic solvent is dimethylformamide (DMF).

26. A method for synthesizing dianhydrogalactitol (DAG) comprising the steps of:

(a) substituting the 1,6-hydroxyl groups of dulcitol with bromine;

(b) substituting the hydroxyl groups of dulcitol other than the 1,6-hydroxyl groups with acetyl groups to yield an intermediate in which the 1,6-hydroxyl groups of dulcitol are substituted with bromine and the hydroxyl groups of dulcitol other than the 1,6-hydroxyl groups are substituted with acetyl groups;

(c) reacting the intermediate of step (b) with zinc in the presence of an organic base to form double bonds through an elimination reaction;

(d) removing the protective acetyl groups; and (e) forming DAG by the Sharpless epoxidation reaction.

27. The method of claim 26 wherein the organic base is sodium methoxide.

28. The method of claim 26 wherein the substitution of the 1,6 hydroxy groups is performed with reaction with acetyl bromide.

29. The method of claim 27 wherein the acetylation of the hydroxy groups other than the 1,6-hydroxy groups is performed with acetic anhydride in pyridine.

* * * * *